United States Patent
Foster et al.

(10) Patent No.: US 8,543,224 B2
(45) Date of Patent: Sep. 24, 2013

(54) ACTIVE FIXATION LEAD WITH HELIX SECUREMENT MECHANISM

(75) Inventors: Arthur J. Foster, Centerville, MN (US); Kimberly A. Jorgensen, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 398 days.

(21) Appl. No.: 12/818,685

(22) Filed: Jun. 18, 2010

(65) Prior Publication Data

US 2010/0331937 A1  Dec. 30, 2010

Related U.S. Application Data

(60) Provisional application No. 61/221,709, filed on Jun. 30, 2009.

(51) Int. Cl.
*A61N 1/00* (2006.01)

(52) U.S. Cl.
USPC .......................................... 607/127

(58) Field of Classification Search
USPC .................................. 607/127, 128
See application file for complete search history.

(56) References Cited

U.S. PATENT DOCUMENTS

| | | | |
|---|---|---|---|
| 4,463,765 A * | 8/1984 | Gold | 607/127 |
| 4,541,681 A | 9/1985 | Dorman et al. | |
| 6,381,500 B1 * | 4/2002 | Fischer, Sr. | 607/127 |
| 6,501,990 B1 * | 12/2002 | Sundberg et al. | 607/122 |
| 6,813,521 B2 * | 11/2004 | Bischoff et al. | 607/122 |
| 7,162,310 B2 | 1/2007 | Doan | |
| 7,369,901 B1 | 5/2008 | Morgan et al. | |
| 2010/0305672 A1 | 12/2010 | Felling et al. | |

* cited by examiner

*Primary Examiner* — Christopher D Koharski
*Assistant Examiner* — Elizabeth K So
(74) *Attorney, Agent, or Firm* — Faegre Baker Daniels LLP

(57) ABSTRACT

An implantable lead may have a distal assembly including a coupler and a fixation helix secured to the coupler. The coupler may include a helical groove that is configured to accommodate the fixation helix. The helical groove may facilitate attaching the fixation helix to the coupler by threading the fixation helix into the helical groove. A weld may provide a secondary attachment between the fixation helix and the coupler.

11 Claims, 5 Drawing Sheets

ACTIVE FIXATION LEAD WITH HELIX SECUREMENT MECHANISM

CROSS-REFERENCE TO RELATED APPLICATIONS

This application claims benefit of U.S. Provisional Application No. 61/221,709, filed on Jun. 30, 2009, entitled "Active Fixation Lead with Helix Securement Mechanism," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is an implantable lead that has a flexible body, a connector assembly that is secured to a proximal end of the body for coupling the lead to an implantable medical device, a conductor member disposed longitudinally within the body and a distal assembly coupled to a distal end of the body. The connector assembly includes a terminal pin that is rotatable relative to the body. The conductor member is coupled to the terminal pin and is rotatable relative to the body. The distal assembly includes a housing having a distal region and a proximal region, the proximal region fixedly coupled to the distal end of the body. A coupler is rotatably disposed within the housing, the coupler having a proximal end and a distal end, the proximal end connected to the conductor member. A helical electrode including a fixation portion and an attachment portion is secured to the coupler and extends distally therefrom, the helical electrode formed of a filar having a circular cross-sectional profile. The distal region of the coupler includes an outer surface defining a helical groove configured to engage the attachment portion of the helical electrode such that the attachment portion of the helical electrode can be threaded onto the distal region of the coupler. A weld further secures the helical electrode to the coupler. The terminal pin is rotatably engaged with the coupler via the conductor member such that rotation of the terminal pin causes the coupler and the helical electrode to rotate and therefore translate relative to the housing.

In Example 2, the implantable lead of Example 1 in which the helical groove has a semi-circular cross sectional profile having a radius that is about the same as a radius of the filar.

In Example 3, the implantable lead of Example 1 or Example 2 in which the helical groove has a pitch that is about the same as a pitch of the attachment portion of the fixation helix.

In Example 4, the implantable lead of Example 1 or Example 2 in which the helical groove has a pitch that is slightly different than a pitch of the attachment portion of the fixation helix.

In Example 5, the implantable lead of any of Examples 1-4 in which the distal region of the coupler has an outer diameter that is about equal to an inner diameter of the attachment portion of the fixation helix.

In Example 6, the implantable lead of any of Examples 1-4 in which the distal region of the coupler has an outer diameter that is slightly greater than an inner diameter of the fixation helix.

In Example 7, the implantable lead of any of Examples 1-6 in which the distal region of the coupler includes a reduced diameter distal end.

Example 8 is an implantable lead that is configured to carry an electrical signal. The implantable lead includes a flexible body that extends between a proximal end and a distal end and that is configured to carry an electrical signal from the proximal end to the distal end, and a distal assembly coupled to the distal end of the body. The distal assembly includes a housing having a distal region and a proximal region, the proximal region fixedly coupled to the distal end of the body. A coupler is rotatably disposed within the housing, the coupler having a proximal end and a distal end, the proximal end connected to the conductor member. A fixation helix having an attachment portion and a fixation portion is fixedly secured to the coupler. A first securement secures the fixation helix to the coupler and provides tensile strength to the attachment of the fixation helix to the coupler and a second securement secures the fixation helix to the coupler and provides torsional strength to the attachment of the fixation helix to the coupler.

In Example 9, the implantable lead of Example 8 in which the second securement is different from the first securement.

In Example 10, the implantable lead of Example 8 or Example 9 in which the distal region of the coupler includes a helical groove complementary to the attachment portion of the fixation helix, and the first securement includes a threaded coupling between the attachment portion of the fixation helix and the distal region of the coupler.

In Example 11, the implantable lead of any of Examples 8-10 in which the second securement includes a weld between the attachment portion of the fixation helix and the distal region of the coupler.

In Example 12, the implantable lead of any of Examples 8-11 in which the fixation helix is formed from a filar having a circular or at least substantially circular cross-sectional profile.

In Example 13, the implantable lead of any of Examples 8-12 in which the attachment portion of the fixation helix has an attachment pitch and the fixation portion of the fixation helix has a fixation pitch, and the attachment pitch is less than the fixation pitch.

In Example 14, the implantable lead of any of Examples 8-13 in which the first securement functions as a primary attachment while the second securement functions as a secondary attachment.

In Example 15, the implantable lead of any of Examples 8-14 in which the coupler includes a first material and the fixation helix includes a second material that does not weld well to the first material.

In Example 16, the implantable lead of any of Examples 8-15 in which the first securement provides a first electrical contact between the coupler and the fixation helix and the second securement provides a second electrical contact between the coupler and the fixation helix.

Example 17 is a method of assembling an extendable/retractable fixation helix for an implantable lead. The method includes providing a fixation helix and a coupler. The fixation helix has a fixation portion and an attachment portion, the attachment portion having a helical pitch. The coupler has a distal region and a proximal region, the distal region including an outer surface defining a helical indentation that is complementary to the attachment portion of the fixation helix. The attachment portion of the fixation helix is threaded onto the distal region of the coupler to provide tensile strength and is then welded to the coupler to provide torsional strength.

In Example 18, the method of Example 17 in which the helical indentation has a pitch that is about equal to a pitch of the attachment portion of the fixation helix.

In Example 19, the method of Example 17 or Example 18, further including securing the proximal region of the coupler to a conductive member.

In Example 20, the method of any of Examples 17-19, further including a subsequent step of disposing the coupler and attached fixation helix into a lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
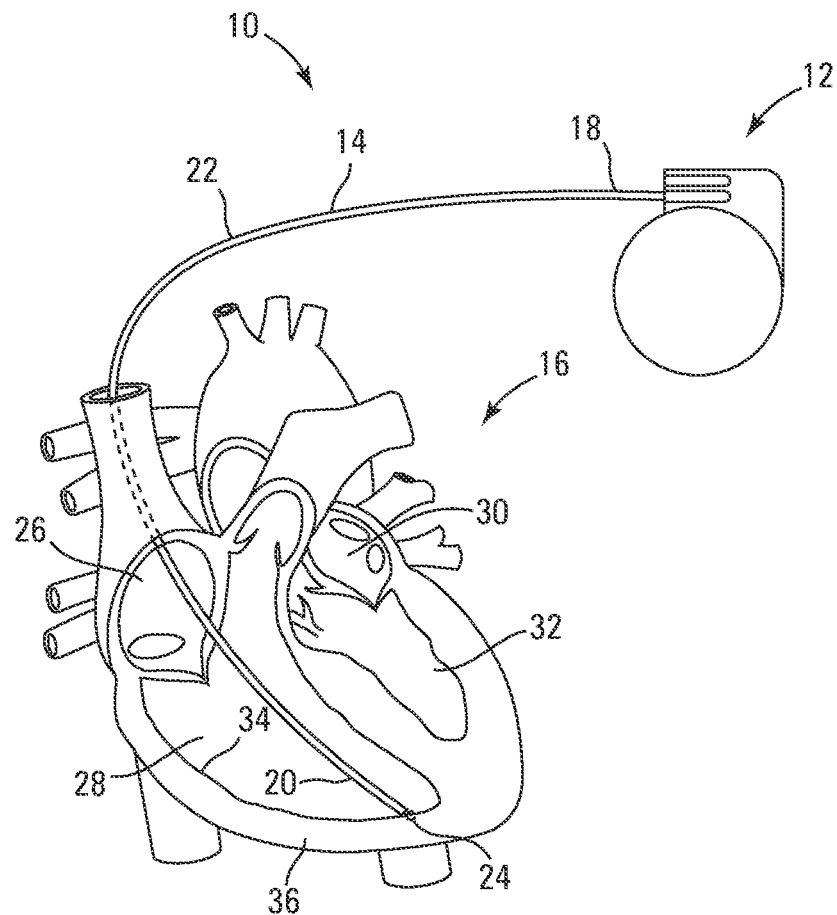
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes an extendable/retractable fixation helix 24, which as will be discussed in greater detail below locates and/or secures the distal region 20 within the heart 16. As will be explained in detail below, the distal region 20 of the lead 14 includes an improved configuration for attaching the fixation helix 24 and other internal components of the lead 14, providing tensile and torsional strength to the attachment of the fixation helix 24.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 and/or to apply a stimulating pulse to the right ventricle 28. In other embodiments, the fixation helix 24 is not electrically active. Rather, in some embodiments, other components of the lead 14 are electrically active.

Figure 2:
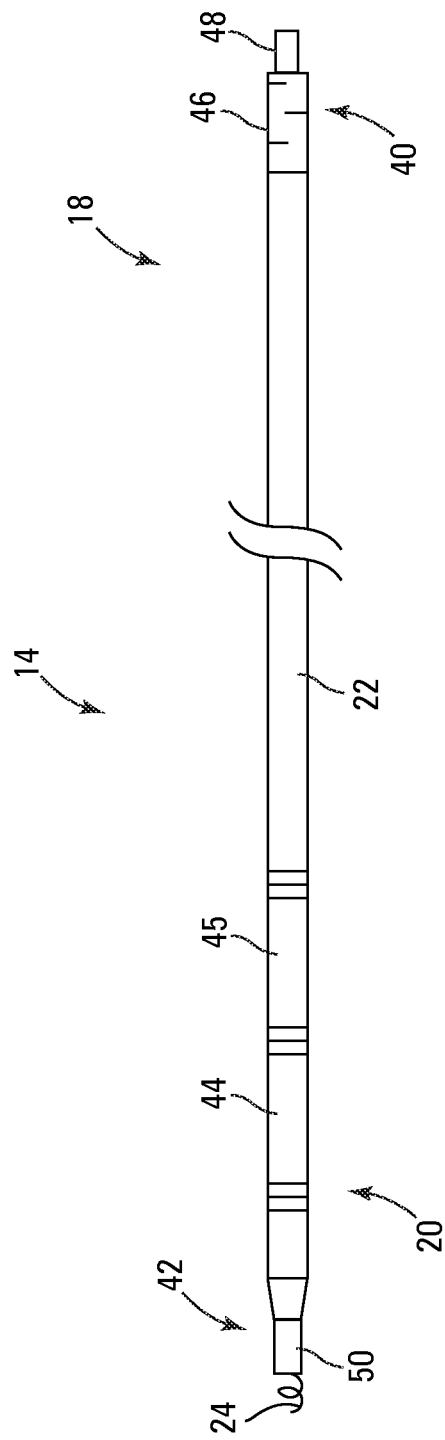
FIG. 2 is a side elevation view of the lead of FIG. 1.

FIG. 2 is an isometric illustration of the lead 14 according to one embodiment. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally within the lead body 22 and which is rotatable relative to the lead body 22 such that rotating the terminal pin 48 (relative to the lead body 22) causes the conductor member to rotate within the lead body 22 as well. In some embodiments, the terminal pin 48 includes an aperture extending therethrough, and the conductor member defines a longitudinal lumen in communication with the aperture. When present, the aperture and/or conductor lumen are configured to accommodate a guide wire or an insertion stylet for delivery of the lead 14.

The distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, tungsten, tantalum, iridium, platinum, titanium, palladium, stainless steel, as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

Figure 3A:
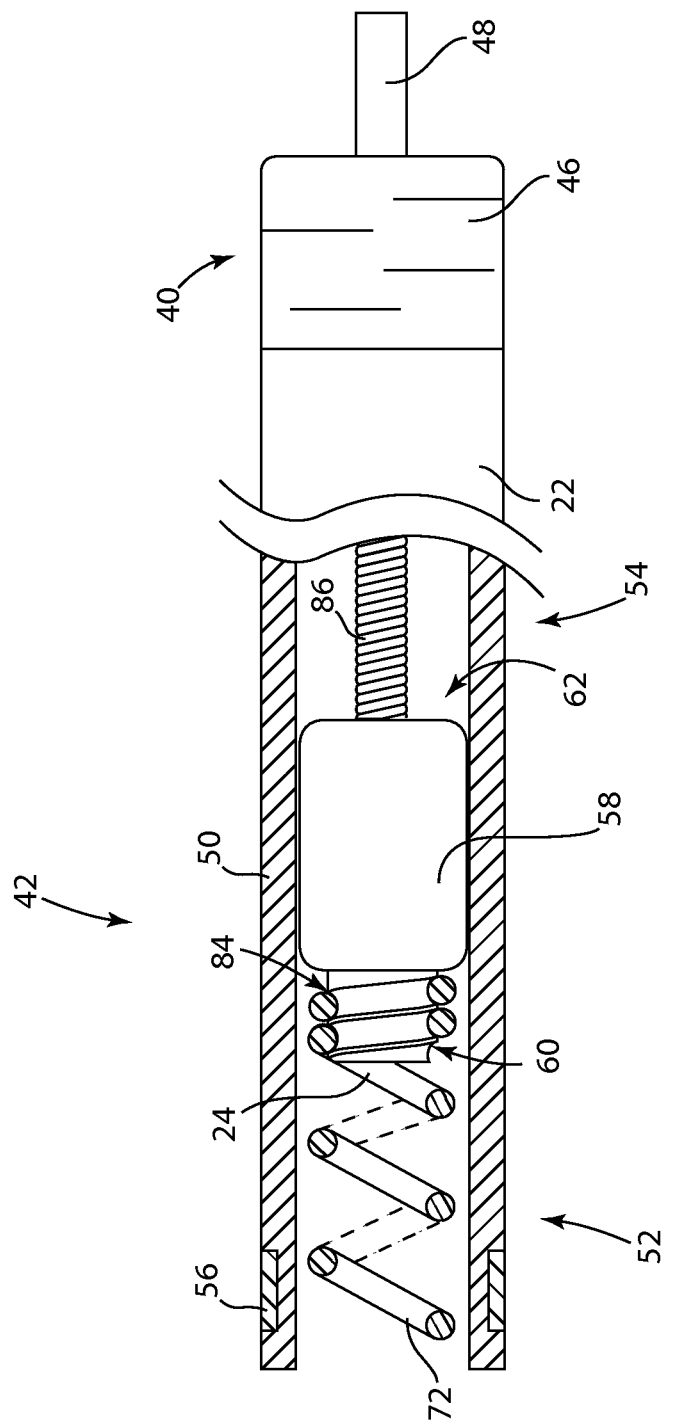
FIG. 3A is a partial cross-sectional view of the lead of FIG. 1, shown in a retracted position.
Figure 3B:
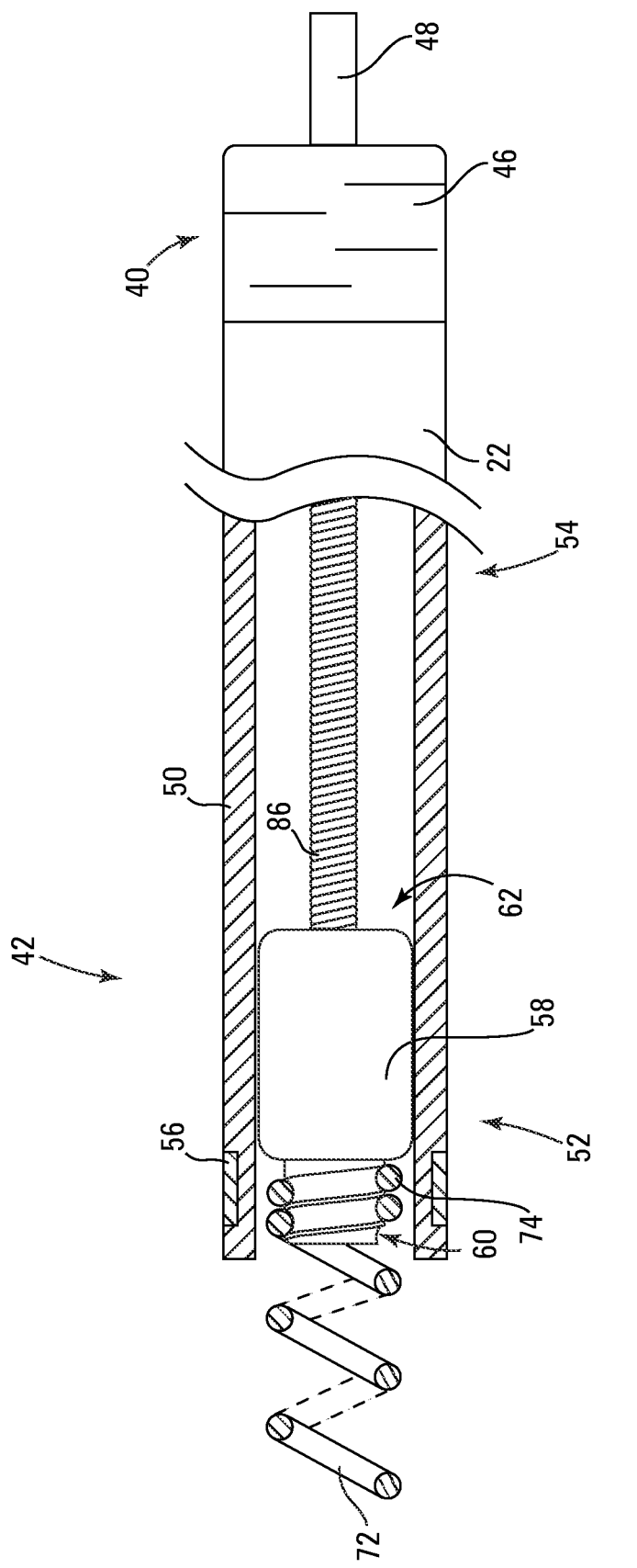
FIG. 3B is a partial cross-sectional view of the lead of FIG. 1, shown in an extended position.

FIGS. 3A and 3B illustrate an embodiment of a lead including distal assemblies in accordance with one embodiment of the present invention. FIGS. 3A and 3B are partial cross-sections of the lead 14 that include the distal assembly 42. In FIG. 3A, the fixation helix 24 is illustrated in a retracted position while FIG. 3B illustrates the fixation helix 24 in an extended position. In the illustrated embodiment, the fixation helix 24 is electrically active so as to be operable as a pace/sense electrode.

As shown in FIGS. 3A and 3B, the housing 50 includes a distal region 52 and a proximal region 54. The housing 50 is, in general, relatively rigid or semi-rigid. In some embodiments, the housing 50 is made of an electrically conductive material such as Elgiloy, MP35N, tungsten, tantalum, iridium, platinum, titanium, palladium, stainless steel, as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 56.

As shown, the distal assembly 42 includes a coupler 58. In some embodiments, the coupler 58 is made of an electrically conductive material such as Elgiloy, MP35N, tungsten, tantalum, iridium, platinum, titanium, palladium, stainless steel, as well as alloys of any of these materials. In some embodiments, the coupler 58 is made of a non-electrically conductive material such as PES (polyethersulfone), polyurethane-based thermoplastics, ceramics, polypropylene and PEEK (polyetheretherketone).

In some embodiments, the coupler 58 is configured to move longitudinally and/or rotationally with respect to the housing 50. As illustrated, the coupler 58 includes a distal portion 60 and a proximal portion 62. As shown, the fixation helix 24 is connected to the distal portion 60 of the coupler 58. In some embodiments, as illustrated, the distal portion 60 may have a relatively smaller diameter that is configured to accommodate the fixation helix 24. In some embodiments, the proximal portion 62 of the coupler 58 may be configured to accommodate a seal (not illustrated).

A conductor member 86 is secured to the proximal portion 62 of the coupler 58, and extends proximally through the lead body 22 to the connector assembly 40. In some embodiments, the conductor member 86 includes or is otherwise formed from a metallic coil. The coupler 58 provides an electrical connection between the conductor member 86 and the fixation helix 24. In some embodiments, the conductor member 86 is welded or soldered to the proximal portion 62 of the coupler 58. In the connector assembly 40, the conductor member 86 is coupled to the terminal pin 48 such that rotation of the terminal pin 48 causes the conductor member 86 to rotate. As the conductor member 86 rotates, the coupler 58 and the fixation helix 24 will also rotate. In some embodiments, the fixation helix 24 is rotated via a stylet that is inserted through an aperture that may be formed within the terminal pin 48 (FIG. 2).

The particular arrangement illustrated in FIGS. 3A and 3B for facilitating extension and retraction of the fixation helix 24 is exemplary only. In other words, any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Provisional Patent Application 61/181,954, the disclosure of which is incorporated by reference herein in its entirety. In other embodiments, a different arrangement for extending and retracting the fixation helix 24 is utilized.

In some embodiments, the fixation helix 24 may be considered as including a fixation portion 72 having an open pitch and an attachment portion 74 having a closed or relatively closed pitch. As shown, for example, in FIG. 4, the attachment portion 74 has a closed pitch in which the adjacent individual turnings of the fixation helix 24 are in close contact with each other while the fixation portion 72 has an open pitch in which the adjacent individual turnings of the fixation helix 24 are spaced apart. In some embodiments, at least a portion of the fixation portion 72 is configured to penetrate the heart muscle or other attachment tissue while the at least a portion of the attachment portion 74 is configured to be attached to the coupler 58.

Figure 4:
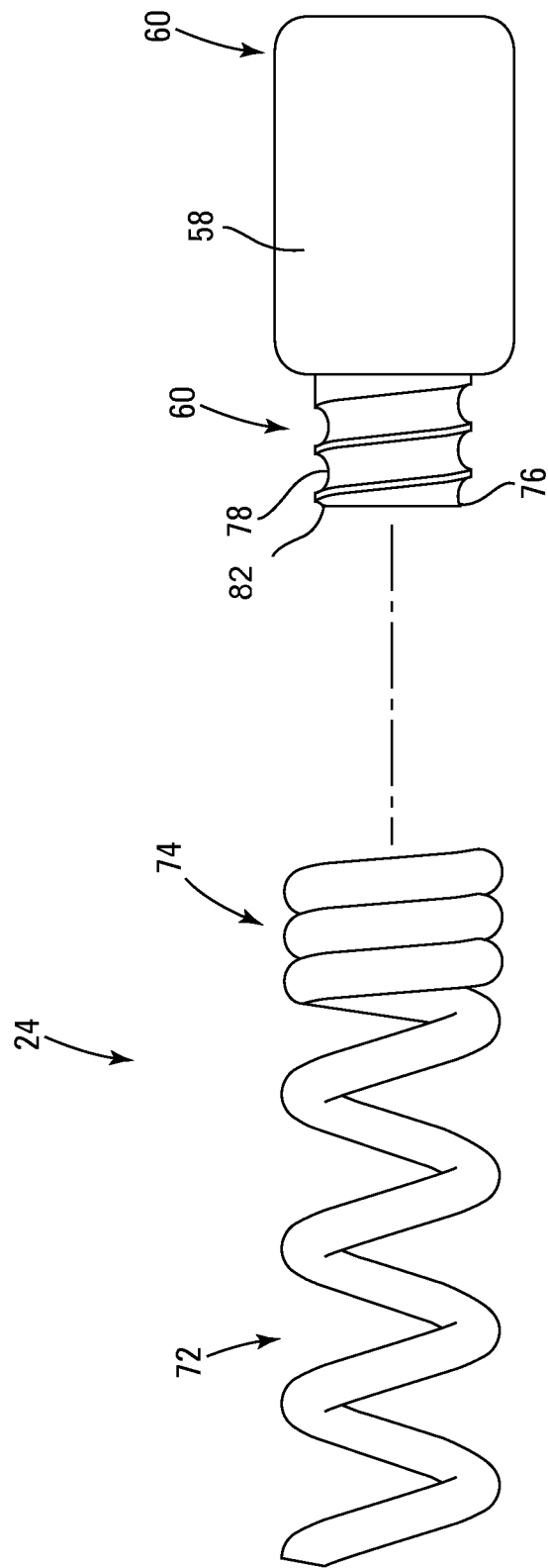
FIG. 4 is an exploded cross-sectional view of a coupler and fixation helix assembly used within the lead of FIG. 1.

In some embodiments, as best illustrated in FIG. 4, the distal portion 60 of the coupler 58 includes an outer surface 76. A helical groove 78 is formed within and/or defined by the outer surface 76. As can be seen by comparing the attachment portion 74 of the fixation helix 24 and the distal portion 60 of the coupler 58, the helical groove 78 is configured to threadedly accommodate the attachment portion 74 of the fixation helix 24. In some embodiments, the distal portion 60 of the coupler 58 includes a lead-in 82 that facilitates threading the fixation helix 24 onto the coupler 58. In some embodiments, the fixation helix 24 is formed from a filar having a circular cross-sectional profile, and the helical groove 78 has a semi-circular profile having a radius that is about the same as a radius of the filar forming the fixation helix 24. In some embodiments, in order to facilitate attachment of the fixation helix 24 to the coupler 58, the helical groove 78 has a pitch that is about the same as a pitch of the attachment portion 74 of the fixation helix 24. In some embodiments, the distal region 60 of the coupler 58 has an outer diameter that is about equal to an inner diameter of the attachment portion 74 of the fixation helix 24.

In one embodiment, the helical groove 78 has a pitch that is slightly different from that of the attachment portion 74 of the fixation helix 24, which can tend to increase the mechanical strength of the attachment of the fixation helix 24 to the coupler 58. In some embodiments, the distal region 60 of the coupler 58 has an outer diameter that is slightly greater than an inner diameter of the fixation helix 24. For example, the distal region 60 of the coupler 58 may have an outer diameter that is about 1 to about 5 percent larger than the inner diameter of the fixation helix 24. As a result, the attachment portion 74 of the fixation helix 24 will be expanded as it is threaded onto the distal portion 60 of the coupler 58, and will tend to apply a compressive force on the distal portion 60 of the coupler 58. This also tends to increase the mechanical strength of the attachment of the fixation helix 24 to the coupler 58.

In some embodiments, as illustrated, the fixation helix 24 may be attached to the coupler 58 using two different attachment methods or techniques. In some embodiments, a first securement secures the fixation helix 24 to the coupler 58, thereby providing tensile strength to the attachment between the fixation helix 24 and the coupler 58. A second securement may secure the fixation helix 24 to the coupler 58 and may be considered as providing torsional strength to the aforementioned attachment. In some embodiments, the first securement provides a first electrical contact between the fixation helix 24 and the coupler 58 and the second securement provides a second electrical contact between the fixation helix 24 and the coupler 58.

In some embodiments, as discussed above, the first securement may be considered as being the threaded engagement between the fixation helix 24 and the coupler 58. In some cases, the second securement may be considered as being a weld 84 that further secures the fixation helix 24 to the coupler 58. In some embodiments, the weld 84 may be considered as providing a secondary attachment between the fixation helix 24 and the coupler 58 while the threaded engagement provides a primary attachment.

The configuration of the fixation helix 24 and the coupler 58 facilitate a primary securement or attachment that provides tensile strength to the attachment between the fixation helix 24 and the coupler 58 as well as a secondary securement or attachment that provides torsional strength to the aforementioned attachment. In some embodiments, the threaded engagement and weld 84, in combination, provide a redundant electrical connection between the fixation helix 24 and the coupler 58. The threaded engagement between the fixation helix 24 and the coupler 58 improves the connection therebetween and provides manufacturing advantages.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. An implantable lead comprising:
    a flexible body extending between a proximal end and a distal end;
    a connector assembly secured to the proximal end for coupling the lead to an implantable medical device, the connector assembly including a terminal pin rotatable relative to the body;
    a conductor member disposed longitudinally within the body and coupled to the terminal pin, the conductor member rotatable relative to the body; and
    a distal assembly coupled to the distal end of the body and including:
        a housing having a distal region and a proximal region, the proximal region fixedly coupled to the distal end of the body;
        a helical electrode including a fixation portion and an attachment portion, the helical electrode formed of a filar having a circular cross-sectional profile;
        a coupler rotatably disposed within the housing, the coupler having a proximal region and a distal region, the proximal region connected to the conductor member, the distal region of the coupler including an outer surface defining a helical groove complementary to the attachment portion of the helical electrode such that the attachment portion of the helical electrode can be threaded onto the distal region of the coupler; and
        a weld further securing the attachment portion of the helical electrode to the distal region of the coupler;
    wherein the terminal pin is rotatably engaged with the coupler via the conductor member such that rotation of the terminal pin causes the coupler and the helical electrode to rotate and therefore translate relative to the housing.

2. The implantable lead of claim 1, wherein the helical groove has a semi-circular cross sectional profile having a radius that is about the same as a radius of the filar.

3. The implantable lead of claim 1, wherein the helical groove has a pitch that is about the same as a pitch of the attachment portion of the helical electrode.

4. The implantable lead of claim 1, wherein the helical groove has a pitch that is slightly different than a pitch of the attachment portion of the helical electrode.

5. The implantable lead of claim 1, wherein the distal region of the coupler has an outer diameter that is about equal to an inner diameter of the attachment portion of the helical electrode.

6. The implantable lead of claim 1, wherein the distal region of the coupler has an outer diameter that is slightly greater than an inner diameter of the helical electrode.

7. The implantable lead of claim 1, wherein the distal region of the coupler comprises a reduced diameter distal end.

8. A method of assembling an extendable/retractable fixation helix for an implantable lead, the method comprising:
    providing a fixation helix having a fixation portion and an attachment portion, the attachment portion having a helical pitch;
    providing a coupler having a distal region and a proximal region, the proximal region configured for attachment to a conductive member, the distal region including an outer surface defining a helical groove complementary to the attachment portion of the fixation helix;

threading the attachment portion of the fixation helix onto the distal region of the coupler to provide tensile strength; and subsequently welding the attachment portion of the fixation helix to the distal region of the coupler to provide torsional strength.

9. The method of claim 8, wherein the helical groove has a pitch that is about equal to a pitch of the attachment portion of the fixation helix.

10. The method of claim 8, further comprising securing the proximal region of the coupler to a conductive member.

11. The method of claim 8, further comprising a subsequent step of disposing the coupler and attached fixation helix into a lead body.

* * * * *